(12) United States Patent
Marze

(10) Patent No.: US 6,833,137 B1
(45) Date of Patent: Dec. 21, 2004

(54) PROTECTION AGAINST TERMITES

(75) Inventor: Xavier Marze, Lyons (FR)

(73) Assignee: Bayer CropScience S.A., Lyons (FR)

(*) Notice: Subject to any disclaimer, the term of this patent is extended or adjusted under 35 U.S.C. 154(b) by 0 days.

(21) Appl. No.: 09/180,477

(22) PCT Filed: May 7, 1997

(86) PCT No.: PCT/FR97/00816

§ 371 (c)(1),
(2), (4) Date: Feb. 5, 1999

(87) PCT Pub. No.: WO97/42817

PCT Pub. Date: Nov. 20, 1997

(30) Foreign Application Priority Data

May 10, 1996 (FR) .............................. 96 06179

(51) Int. Cl.$^7$ .............................................. A01N 25/34
(52) U.S. Cl. .................... 424/413; 424/403; 424/405; 424/406; 424/409; 424/411; 424/412; 424/DIG. 11; 514/407; 523/122
(58) Field of Search ................. 424/DIG. 11, 403, 424/405–407, 409, 411–413; 523/122; 514/404, 407

(56) References Cited

U.S. PATENT DOCUMENTS

| | | | |
|---|---|---|---|
| 5,232,940 A | 8/1993 | Hatton et al. .............. | 514/407 |
| 5,306,694 A | 4/1994 | Phillips et al. ............. | 504/253 |
| 5,451,598 A | 9/1995 | Salmon et al. ............. | 314/404 |
| 5,747,519 A | 5/1998 | Kodama et al. ............ | 514/407 |

FOREIGN PATENT DOCUMENTS

| | | |
|---|---|---|
| DE | 2438365 | 2/1976 |
| EP | 0295117 | 12/1988 |
| EP | 0500209 | 8/1992 |
| JP | 08/108403 | 4/1996 |
| WO | 87/03781 | 7/1987 |
| WO | 93/06089 | 4/1993 |
| WO | 94/21606 | 9/1994 |
| WO | 95/18532 | 7/1995 |
| WO | 95/22902 | 8/1995 |
| WO | 9747190 | * 12/1997 |

OTHER PUBLICATIONS

Database WPI, Section Ch, Week 9627, Derwent Publications Ltd., AN96–263151 (1996)—abstract of JP 08/108403.

Database WPI, Section Ch, Week 9605, Derwent Publications Ltd., AN96–045270 (1996)—abstract of JP 07/309701.

Database WPI, Section Ch, Week 9216, Derwent Publications Ltd., AN92–127223 (1992)—abstract of JP 04/069301.

Patent Abstracts of Japan, vol. 17, No. 53, M–1361 (1993)—abstract of JP 04/265345.

* cited by examiner

Primary Examiner—Neil Levy
(74) Attorney, Agent, or Firm—Connolly Bove Lodge & Hutz LLP

(57) ABSTRACT

The invention features a composite material comprising a gypsum partitional slab coated on at least one of its two surfaces with a cardboard or paper ply, the ply being impregnated with a 1-phenylpyrazole insecticide, preferably 5-amino-3-cyano-1-(2,6-dichloro-4-trifluoromethylphenyl)-4-trifluoromethylsulfinylpyrazole. The invention provides an insect protection method for dwellings against the damage caused by borers, especially termites comprising fixing the composite material on at least 50%, preferably 95%, of the total surface area of the internal face of partitions and walls.

12 Claims, No Drawings

PROTECTION AGAINST TERMITES

The present invention relates to the field of gypsum-based composite construction materials and more specifically to gypsum blocks, also known under the name of plasterboard. Another subject of the invention is a method for the protection of dwellings against damage caused by insects of perforating type, and also the dwellings thus protected.

Gypsum blocks are widely known and used in the construction and fitting out of residential buildings. Within the meaning of the present invention, gypsum blocks is understood to mean a composite material comprising a gypsum board covered on at least one of its faces, preferably on both, with a sheet of cardboard or paper. Gypsum blocks are usually fixed to the crude material used for the construction of partitions and walls and more specifically to the wall of the said material situated inside the dwellings, whatever the material from which these partitions or walls are constructed: concrete, bricks or other. The surface condition of these blocks makes possible rapid finishing of the partition or wall thus obtained, in particular as regards the application of a coating and/or of paint and/or of wallpaper.

Moreover, it is known that these gypsum blocks are particularly liable to be attacked by insects, in particular by insects of perforating type and more particularly by termites. In point of fact, damage caused to dwellings by these insects, and particularly by termites, can be quite considerable. Indeed, termites in particular are capable of moving inside the construction materials of dwellings and of rendering them brittle, due to the fact that they feed thereon. This damage can become more serious as the termites accomplish their work of destruction without being detected, until the said work finally ends in causing irreparable damage to the dwelling. Moreover, as mentioned above, termites move in parts of dwellings which are virtually impossible to access, making direct treatment of the said termites virtually impossible.

Wooden parts of buildings, such as frameworks or panelling, in particular window frames and door frames, are more especially exposed to damage caused by these insects.

There thus exists a need to have available gypsum blocks which are protected against insects, in particular termites.

Another aim of the invention is to provide gypsum blocks which are resistant to insects, in particular to termites.

Another aim of the invention is to provide gypsum blocks which prevent termites from moving along in tunnels which they hollow out inside construction components.

Another aim of the invention is to provide gypsum blacks comprising a small amount of insecticidal compound.

Another aim of the invention is to meet the existing requirements as regards the protection of dwellings against damage caused by termites.

Another aim of the invention is to provide dwellings protected against termites.

It has now been found that these aims could be achieved in all or in part by virtue of the composite material according to the invention.

The invention consequently relates to a composite material comprising a gypsum board covered on at least one of its 2 faces with a sheet made of cardboard or paper, characterized in that the sheet, or each of the sheets, comprises, as insecticidal active material, a 1-arylpyrazole, of formula (I):

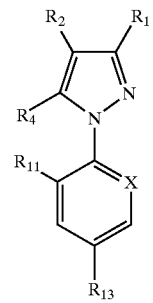
(I)

in which:

$R_1$ is a halogen atom or a CN or methyl group;

$R_2$ is $S(O)_n R_3$;

$R_3$ is alkyl or haloalkyl;

$R_4$ represents a hydrogen or halogen atom or an $NR_5 R_6$, $S(O)_m R_7$, $C(O)R_7$ or $C(O)O—R_7$, alkyl, haloalkyl or $OR_8$ radical or an $—N=C(R_9)(R_{10})$ radical;

$R_5$ and $R_6$ independently represent a hydrogen atom or an alkyl, haloalkyl, C(O)alkyl or $S(O)_r CF_3$ radical or $R_5$ and $R_6$ can together form a divalent alkylene radical which can be interrupted by one or two divalent heteroatoms, such as oxygen or sulphur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted by one or a number of halogen atoms or groups such as OH, —O-alkyl, —S-alkyl, cyano or alkyl;

X represents a trivalent nitrogen atom or a $C—R_{12}$ radical, the other three valencies of the carbon atom forming part of the aromatic ring;

$R_{11}$ and $R_{12}$ represent, independently of one another, a hydrogen or halogen atom;

$R_{13}$ represents a halogen atom or a haloalkyl, haloalkoxy, $S(O)_q CF_3$ or $SF_5$ group;

m, n, q and r represent, independently of one another, an integer equal to 0, 1 or 2;

with the proviso that, when $R_1$ is methyl, then $R_3$ is haloalkyl, $R_4$ is $NH_2$, $R_{11}$ is Cl, $R_{13}$ is $CF_3$ and X is N.

In the present text, it is clearly understood that the alkyl radicals of the definition of the formula (I) are, except when otherwise defined, radicals with a straight or branched chain generally comprising from 1 to 6 carbon atoms. The ring formed by the divalent alkylene radical representing $R_5$ and $R_6$ and by the nitrogen atom to which $R_5$ and $R_6$ are attached is generally a 5-, 6- or 7-membered ring.

A preferred class of compounds of formula (I) is composed of the compounds such that $R_1$ is CN and/or $R_3$ is haloalkyl and/or $R_4$ is $NH_2$ and/or $R_{11}$ and $R_{12}$ are, independently of one another, a halogen atom and/or $R_{13}$ is haloalkyl.

A compound of formula (I) which is very particularly preferred in the invention is

hereinafter known as compound A.

According to a preferred alternative form of the invention, the gypsum board is covered on both its faces with a sheet of cardboard or paper, at least one of these sheets, preferably both, comprising the insecticidal active material.

The gypsum board generally has a thickness of between 0.5 and 5 cm, preferably between 0.6 and 2 cm, and the cardboard or the paper used to cover one of its faces (or both) usually have a relative density of between 50 and 500 g/m$^2$, preferably between 150 and 250 g/m$^2$.

The thickness of the cardboard or paper sheet or sheets is generally between 0.1 and 10 mm, preferably between 0.2 and 5 mm.

The gypsum block according to the invention, although comprising an amount of the compound of formula (I) localized only in the thickness of the cardboard (or paper) sheet or sheets, advantageously and in its entirety offers improved protection against termites, in particular as regards the number and the size of the perforations produced by the latter. This improved protection results in particular from the destruction of more than 70%, preferably of more than 95%, of the population of termites attacking the said block.

The amount of compound of formula (I) in the gypsum blocks according to the invention is an amount which is effective against perforations by insects, in particular by termites.

These effective amounts are generally between 0.001 and 10 g/m$^2$, preferably between 0.01 and 2 g/m$^2$. The possibility of obtaining improved protection against termites by means of a small amount of active compound is particularly advantageous.

Compounds of formula (I) can be prepared according to one or other of the processes described in Patent Applications WO 87/3781, 93/6089 or 94/21606 or European Patent Application 295,117 or any other process coming within the competence of the person skilled in the art who is a specialist in chemical synthesis.

The composite material according to the invention can be prepared by at least one of the 2 following methods:

a) Liquid gypsum is poured, depending on the situation, onto 1 cardboard sheet or alternatively between 2 horizontal cardboard (or paper) sheets progressing continuously over rollers and separated by a distance substantially equal to the thickness of the gypsum blocks. At least one of these sheets, preferably both, have been impregnated beforehand with a composition comprising the active material of formula (I). The manufacture continues, in accordance with the known process, with a drying phase.

The composition used for the impregnation is generally a solution of the compound of formula (I) in a solvent, such as propylene glycol, or alternatively a water-emulsifiable concentrate prepared in a known way.

This impregnation can be carried out, for example, by incorporation of the composition in the paper pulp used to manufacture the cardboard or alternatively by passing the cardboard sheet in the dry state into a tank of liquid in which the said composition has been incorporated.

b) Gypsum blocks are manufactured according to a technique known per se. The composition comprising the active material of formula (I) is applied by spraying over the paper or the cardboard covering the external surface or both external surfaces of the said blocks.

Another subject of the invention is a method for the protection of dwellings against damage caused by insects of perforating type, characterized in that a composite material according to the invention is fixed to at least 50%, preferably 95%, of the total surface area of the interior wall of partitions and walls. Due to the effectiveness of the composite material according to the invention against insects of perforating type, in particular against termites, complete dwellings are thus better protected against the attacks of these insects, and in particular the wooden parts which are more particularly exposed to these attacks, whatever their situation in the dwelling.

Termites are the most formidable among the insects of perforating type capable of causing such damage.

A final subject of the invention is a dwelling offering improved protection against insects of perforating type, characterized in that at least 50%, preferably 95%., of the total surface area of the interior wall of its partitions and walls is covered with composite material according to the invention.

The following example, given without implied limitation, illustrates the invention and shows how it can be put into practice.

EXAMPLE

A gypsum block is used which has a surface area of 30 cm$^2$ and a thickness of 0.8 cm and is covered on both its face with cardboard having a relative density of 195 g/m$^3$ and a thickness of 0.2 mm.

A solution of compound A in propylene glycol is sprayed over both faces of this block in an amount such that the gypsum block contains 0.05 g/m$^2$ of compound A.

Two vertical cylindrical chambers with a diameter of 5 cm are separated using the gypsum block thus treated. The upper chamber comprises 160 termites placed in damp compost. The lower chamber comprises a piece of wood placed in moistened sand.

After 21 days, a mortality rate equal to 100% is observed.

What is claimed is:

1. A composite material comprising a gypsum board covered on at least one of its two faces with a sheet made of cardboard or paper, wherein the sheet, or each of the sheets, comprises a termiticidally effective amount of 5-amino-3-cyano-1-(2,6-dichloro-4-trifluoromethylphenyl)-4-trifluoromethylsulfinylpyrazole, wherein the gypsum board has a thickness of between 0.5 and 5 cm, and the cardboard or paper has a relative density of between 50 and 500 g/m$^2$.

2. A composite material according to claim 1, wherein the gypsum board is covered on both of its faces with a sheet of cardboard or paper, at least one of these sheets comprising a termiticidally effective amount of 5-amino-3-cyano-1-(2, 6-dichloro-4-trifluoromethylphenyl)-4-trifluoromethylsulfinylpyrazole.

3. A composite material according to claim 1, wherein the gypsum board is covered on both of its faces with a sheet of cardboard or paper, each of these sheets comprising a termiticidally effective amount of 5-amino-3-cyano-1(2,6-dichloro-4-trifluoromethylphenyl)-4-trifluoromethylsulfinylpyrazole.

4. A composite material according to claim 1, wherein the gypsum board has a thickness of between 0.6 and 2 cm, and the cardboard or paper has a relative density of between 150 and 250 g/m$^2$.

5. A composite material according to claim 1, wherein the thickness of the cardboard or paper sheet or sheets is between 0.1 and 10 mm.

6. A composite material according to claim 5, wherein the thickness of the cardboard or paper sheet or sheets is between 0.2 and 5 mm.

7. A composite material according to claim 1, wherein the termiticidally effective amount of 5-amino-3-cyano-1-(2,6-dichloro-4-trifluoromethylphenyl)-4-trifluoromethylsulfinylpyrazole is between 0.001 and 10 g/m$^2$.

8. A composite material according to claim 7, wherein the termiticidally effective amount of 5-amino-3-cyano-1-(2,6-dichloro-4-trifluoromethylphenyl)-4-trifluoromethylsulfinylpyrazole is between 0.01 and 2 $g/m^2$.

9. A composite material according to claim 1, wherein the gypsum board has a thickness of between 0.6 and 2 cm; the cardboard or paper has a relative density of between 150 and 250 $g/m^2$; the thickness of the cardboard or paper sheet or sheets is between 0.1 and 10 mm; and the termiticidally effective amount of 5-amino-3-cyano-1-(2,6-dichloro-4-trifluoromethylphenyl)-4-trifluoromethylsulfinylpyrazole is between 0.001 and 10 $g/m^2$.

10. A composite material according to claim 9, wherein the thickness of the cardboard or paper sheet or sheets is between 0.2 and 5 mm, and the termiticidally effective amount of 5 amino-3-cyano-1-(2,6-dichloro-4-trifluoromethylphenyl)-4-trifluoromethylsulfinylpyrazole is between 0.01 and 2 $g/m^2$.

11. A method for protecting a dwelling against damage caused by termites, said method comprising fixing a composite material as claimed in claim 1 to at least 50% of the total surface area of the interior wall of partitions and walls.

12. A method according to claim 11, wherein the composite material is fixed to at least 95% of the total surface area of the interior wall of partitions and walls.

* * * * *